(12) United States Patent
Wagner

(10) Patent No.: US 7,808,644 B2
(45) Date of Patent: Oct. 5, 2010

(54) DEVICE FOR OPTICALLY MEASURING THE SHAPES OF OBJECTS AND SURFACES

(75) Inventor: Christoph Wagner, Königsbach (DE)

(73) Assignee: OBE Ohnmacht & Baumgartner GmbH & Co. KG, Ispringen (DE)

( * ) Notice: Subject to any disclaimer, the term of this patent is extended or adjusted under 35 U.S.C. 154(b) by 308 days.

(21) Appl. No.: 11/886,196

(22) PCT Filed: Mar. 23, 2006

(86) PCT No.: PCT/EP2006/002678

§ 371 (c)(1),
(2), (4) Date: Sep. 12, 2007

(87) PCT Pub. No.: WO2006/100077

PCT Pub. Date: Sep. 28, 2006

(65) Prior Publication Data

US 2008/0137088 A1    Jun. 12, 2008

(30) Foreign Application Priority Data

Mar. 24, 2005  (DE) .................... 10 2005 013 614
May 6, 2005    (DE) .................... 10 2005 021 896

(51) Int. Cl.
*G01N 21/86* (2006.01)
(52) U.S. Cl. ....................... 356/446; 356/236
(58) Field of Classification Search ............... 356/236
See application file for complete search history.

(56) References Cited

U.S. PATENT DOCUMENTS

| 4,606,635 | A | 8/1986 | Miyazawa et al. |
| 5,024,525 | A | 6/1991 | Yoshida |
| 5,461,417 | A | 10/1995 | White et al. |
| 5,598,265 | A | 1/1997 | de Groot |
| 5,644,140 | A | 7/1997 | Biedermann et al. |
| 5,777,244 | A | 7/1998 | Kumagai et al. |
| 6,463,393 | B1 * | 10/2002 | Giger .................... 702/97 |
| 6,611,617 | B1 * | 8/2003 | Crampton .............. 382/154 |
| 7,522,277 | B2 * | 4/2009 | Lehn et al. ............ 356/239.1 |
| 2003/0184740 | A1 | 10/2003 | Paradis |
| 2005/0254378 | A1 | 11/2005 | Wagner et al. |

FOREIGN PATENT DOCUMENTS

CN          1147627 A     4/1997

(Continued)

OTHER PUBLICATIONS

Chinese Office Action issued Dec. 16, 2009 in the parallel Chinese procedure for CN 200680009574.9.

(Continued)

*Primary Examiner*—Gregory J Toatley, Jr.
*Assistant Examiner*—Rebecca C Slomski
(74) *Attorney, Agent, or Firm*—Harness, Dickey & Pierce, P.L.C.

(57) ABSTRACT

A device is provided for optically measuring shapes and/or examining objects, comprising at least one camera, at least one lens, a scattering body and at least two light sources. The device is characterized in that the scattering body is opaque and that at least two light sources are disposed on the inside of the scattering body and illuminate the inside thereof, and that either only two light sources are used, which are disposed opposite from one another on an imaginary diameter line, or that the light sources are disposed at the corners of a—preferably equilateral—triangle or a cross.

39 Claims, 17 Drawing Sheets

FOREIGN PATENT DOCUMENTS

| | | |
|---|---|---|
| DE | 40 04 922 A1 | 8/1990 |
| DE | 44 13 832 C2 | 10/1995 |
| DE | 102 17 068 A1 | 5/2004 |
| EP | 1 006 349 A1 | 6/2000 |
| WO | WO-2004/051186 A1 | 6/2004 |

OTHER PUBLICATIONS

International Search Report for PCT/EP2006/002678 dated Jun. 21, 2006 (in German and English).

International Preliminary Report on Patentability for PCT/EP2006/002678, Apr. 7, 2006.

* cited by examiner

DEVICE FOR OPTICALLY MEASURING THE SHAPES OF OBJECTS AND SURFACES

The invention relates to a device for optically measuring the shapes of and/or for examining objects and surfaces. Most methods and devices for optically measuring the shapes of and/or for examining objects and surfaces can be divided into two categories.

Image processing devices, particularly in industrial image processing. These methods are characterized in that within a very short time one or more images of the object are recorded and subsequently automatically examined and evaluated by an electronic processing unit. For this process, times in the range of fractions of a second for imaging, including examination, are common. The measuring of two-dimensional (2D) characteristics in the image plane, such as lengths, angles, surfaces and the like, is state of the art. The measurement and examination of three-dimensional characteristics causes some problems because the recorded images reproduce the third dimension perpendicular to the image plane only insufficiently.

In contrast, devices relating to optical 3D metrology (three-dimensional metrology) specialize in measuring not only the characteristics in the image plane, but also characteristics of the third dimension perpendicular to the image plane. The disadvantage is that these methods are much more time-consuming than imaging methods. For these methods, times of one up to several seconds and minutes are common. Automatic examination of the measurement results is also not common in many cases.

It is the object to unite the advantages of both categories and eliminate the disadvantages. This will allow the verification, measurement and automatic examination of two-dimensional as well as three-dimensional characteristics within a very short time. In this way, a connection is established between the areas of imaging and optical 3D metrology.

In particular shiny objects and surfaces made of metal, plastic and the like are taken into consideration, which are frequently encountered in technical applications. These surfaces are associated with great difficulty due to directed light reflection, both in imaging and optical 3D metrology. However, also diffusely scattering objects are taken into account, which in general do not pose any difficulty.

The analysis and/or measurement of 2D and/or 3D characteristics as well as optionally an automatic examination can be performed with the method described in WO2004/051186. In this method, which is referred to as photometric deflectometry, a photometric stereo method, a deflectometric method and a scattering body S are combined such that the positions on the scattering body surface are encoded across a large area.

A device for performing this known method, for example, has the following design. A camera K comprising a lens Obj is aimed at an object G. The object is illuminated by a scattering body S, which is in turn illuminated by at least one, preferably a plurality of separately switchable light sources or groups of light sources 1, 2, 3 . . . (FIG. 1).

FIG. 1 shows three light sources 1, 2 and 3. These are preferably disposed in a plane extending perpendicular to the image plane of FIG. 1. However, not all are disposed in the image plane of FIG. 1. For example the center light source 3 is offset toward the back from the image plane of FIG. 3.

In the implementation of such a device, a person skilled in the art faces a series of questions:

1. In what position should the light sources 1, 2, 3 . . . be placed to achieve the best possible measurement and examination results?
2. How can bright illumination of the object be achieved?
3. Is it advantageous to bundle the beam of the light source on the object by optics?
4. In what position is the camera K best placed?
5. What dimensions of the sight opening in the scattering body S are advantageous?
6. What material is advantageously used in the production of the scattering body, and what should the surface properties be?
7. How can contamination and mechanical damage to the scattering body, and consequently poor results, be avoided?

The particular difficulty is to find a technical solution, which is equally compatible with all questions. This is particularly difficult because opposing measures are required to solve these questions.

For example, if particular emphasis is placed on question 1, the light sources should be disposed with sufficient distance from the scattering body (FIG. 2). As a result, every point of the light source has substantially the same distance to the scattering body and nearly parallel illumination. In this case, according to the method described in WO 2004/051186 theoretically easy-to-control conditions exist, since both the direction and the distance of the light source can be considered constant. This is particularly important since the areal encoding of the scattering body surface is the result of the interaction between the scattering body inclination and the direction of illumination. Vertically incident light on the respective surface section of the scattering body brings about encoding with excellent brightness and grazing incidence with minimized brightness. It is also significant from what direction the light sources illuminate the scattering body. If these directions are close together, the differences in encoding are small (low sensitivity of the measuring apparatus in relation to the inclination to be measured), if the directions are far apart, the differences are large (high sensitivity). The device will then respond excellently even to minor variations of the local object inclination. However, wide ranges of the scattering body cannot be illuminated at all.

For question 2, on the other hand, a large distance of the light sources is negative. When the distance is doubled, it is to be expected that the brightness level of the scattering body and therefore of the object is reduced by a factor of 4.

This leads to question 3 and whether the light is advantageously bundled. In this way, the brightness level can be maintained even at larger distances. This is in turn contradicted by the fact that the optical installations and reflectors required for bundling generally do not allow the same uniform illumination that is possible in their absence.

Also question 4 must be taken into consideration. The position of the camera should be selected such that it does not produce shading on the scattering body. However, this is particularly the case if the camera is positioned close to the scattering body (FIG. 3). On the other hand, it is desirable to dispose the camera as close to the scattering body and the object as possible, so as to achieve good resolution of the object.

The solution to this question is linked to question 5. At a small distance of the camera, the sight opening in the scattering body can be selected smaller, while at a larger distance it must be selected larger to capture all areas of the object. As a result, however, the scattering body is interrupted across wide areas. These areas are then not available for illuminating the object. If the surface of the object is inclined such that only light from these blank spots of the scattering body can be reflected in the camera, the device is blind to all affected inclinations (FIG. 4).

Questions 6 and 7 relate to the material of the scattering body, the surface properties thereof, contamination and potential mechanical damage. It is conceivable, for example, to use a roughened, transparent plastic (surface scatterer) or a frosted plastic (volume scatterer). Advantageous, uniform scattering in all spatial directions is achieved with the volume scatterer, however a very large amount of light remains unused. Furthermore, undesirable light reflection occurs on the smooth surface. A surface scatterer in turn deflects the path of the light to a lesser degree, allowing more light to be used. The disadvantage is that no uniform emission in all directions is achieved and that a rough surface tends to become polluted by dust and fingerprints and is also difficult to clean. If glass is selected for the scattering body instead of plastic, better properties can be achieved with respect to mechanical stability and cleaning. On the other hand, the precise manufacture of a scattering body with accurate dimensions is much more complex when using glass than plastic. In addition, the glass may break.

Figure 5:
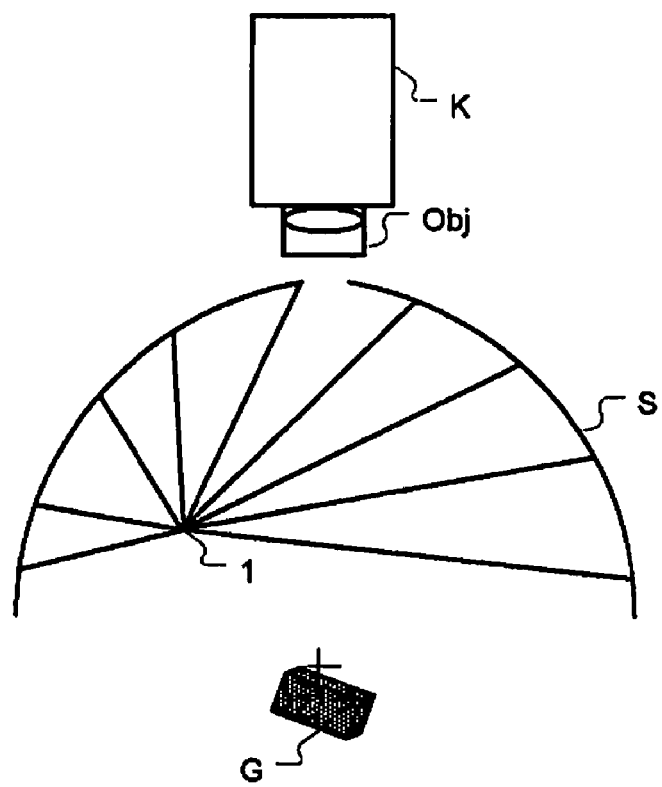
FIG. 5 illustrates a device having an opaque scattering body with a light source on an inside of the scattering body.

All these questions are solved according to the invention as follows: Instead of the transparent scattering body, an opaque scattering body is used, and in addition the light sources are disposed on the inside of the scattering body. This solution is not apparent at all, particularly with respect to the extremely important question 1. The closer a light source is disposed to the scattering body, in extreme cases even inside the scattering body, the less one can assume that the scattering body is illuminated by a bundle of parallel rays. Instead, it can be assumed that the light sources radiate, for example, into the entire hemisphere (FIG. 5). Depending on the light source and radiation characteristic with respect to the direction, the illumination distribution on the scattering body is different. The entire calculative evaluation—as it is apparent from WO 2004/051186—would then be unusable. Also the distance of the light sources to every point of the scattering body varies greatly as a function of the position of the light source. It is not possible to provide the light sources at the center of a spherical scattering body because the center and the surrounding area thereof are reserved for the object to be examined.

Figure 1:
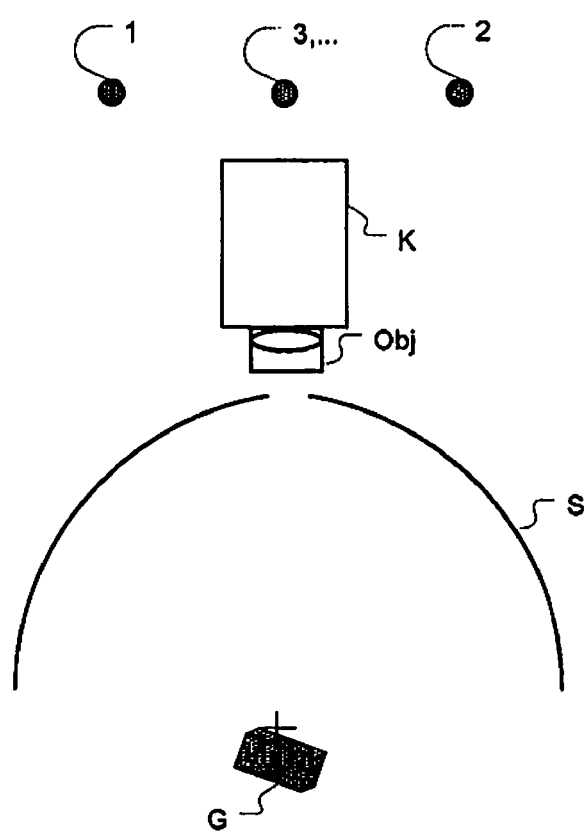
FIG. 1 illustrates a device with illumination of an outside of a scattering body.
Figure 2:
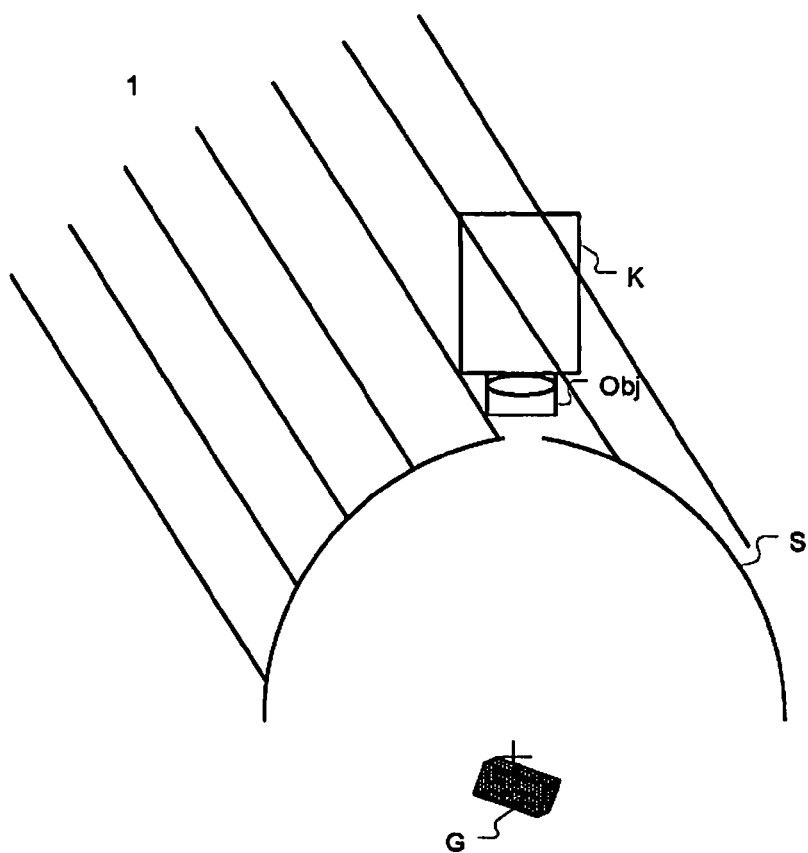
FIG. 2 illustrates a device with illumination of an outside of a scattering body with light sources far removed.
Figure 3:
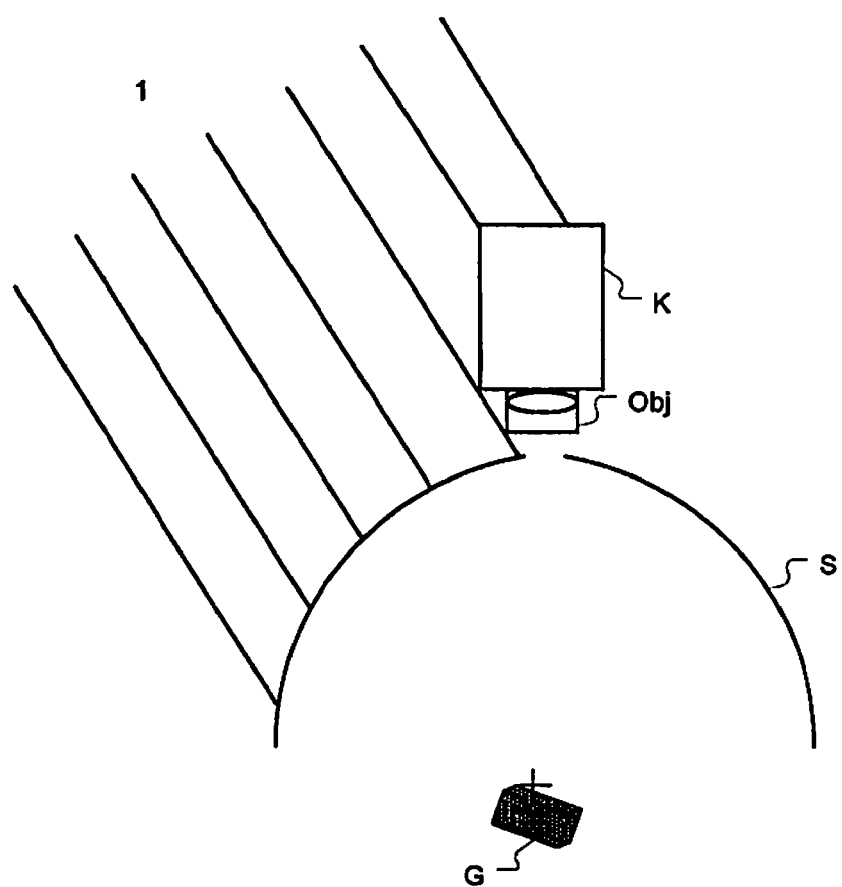
FIG. 3 illustrates the device of FIG. 2 with a camera causing shading or shadowing on the scattering body.
Figure 4:
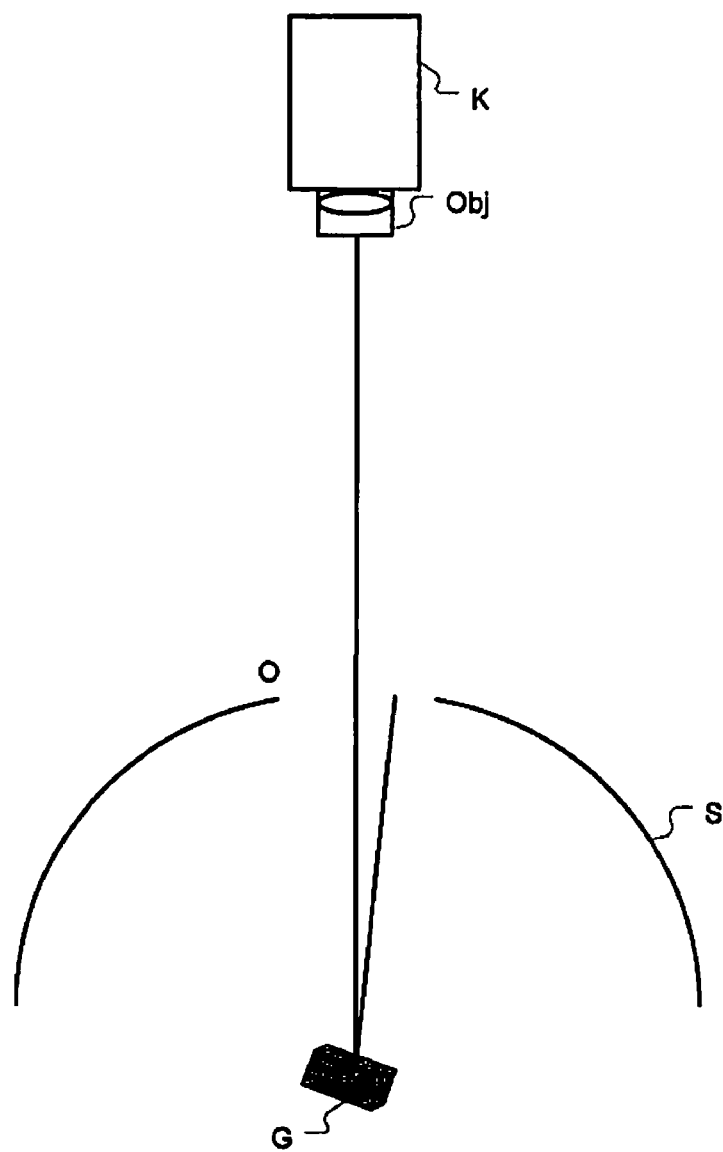
FIG. 4 illustrates a device having a scattering body with a large sight opening.

According to the invention, this problem is solved in that complex influencing factors, such as the direction of illumination on the scattering body, the respective distance of the scattering body and the illuminated surface thereof to the light source and the spatial radiation characteristics of the light source, skillfully compensate each other such that an illumination distribution is simulated as it occurs with external illumination with parallel light incidence (FIG. 2). In light of the large number of mutually dependent parameters, this plan appears nearly hopeless.

According to the invention, however, a solution was found for a special combination of the parameters. Based on the calculative complex correlations, a solution was determined based on a simulation, and the result is presented below.

A light source configured as a Lambert emitter is preferred as the illumination device. This means that the radiant intensity varies as a function of the cosine of the radiation angle. This type of distribution is frequently encountered with illuminated bodies, but not with luminous bodies and light sources. Most frequently, constant irradiation in all spatial directions (such as filament bulbs, gas discharge lamps) or highly directed irratiation in the case of lasers and LEDs is found. The special case of Lambert-type radiation, however, can be achieved with specially designed LEDs.

The shape of the scattering body is preferably configured as a sphere, semi-sphere or parts thereof. The materials used are preferably metal, opaque plastic or other materials, which allow excellent control of the production processes. The critical issue is the proper selection of the position and orientation of the light sources. To orient them on the surface of a hemispherical scattering body, the term 'north pole' is selected for the apex of the hemisphere located on the camera side and the term 'equator' is selected for the edge of the hemisphere. The terms north pole and equator are also used for scattering bodies with other shapes. The light sources are preferably disposed in a plane close to the equator plane. The principal ray should be oriented in relation to the scattering body, for example, at an angle between $-90°$ and $+90°$ in relation to a perpendicular to the equator plane. The angle to the perpendicular is preferably $-30°$ to $+30°$. The lighting conditions are particularly advantageous at an angle of $0°$ or close to $0°$. The principal ray of the light source then either coincides with the perpendicular to the equator plane or encloses a very small angle with the same.

A plurality, preferably four light sources are used, which are preferably disposed in the shape of a cross, for example "+" or "X". The center of the cross is preferably located on a line extending perpendicular to the equator plane and through the center thereof. The light sources are disposed at a certain distance from the center of the scattering body, for example 20% to 80%, preferably 30% to 70% of the distance between the center of the scattering body and the inside surface thereof. In the case of a spherical scattering body, this corresponds to a sphere radius. Particularly advantageous conditions exist around 50% of the sphere radius (FIG. 6).

With respect to the implementation of the light sources 1, 2, 3 and so on, the following should be noted: Preferably, four light sources are provided, which are disposed in one plane. It is conceivable to dispose the light sources in the equator plane of the scattering body S or slightly above or below that. In FIG. 6, the light sources are disposed in a row only apparently. In fact, the light sources 1 and 2 are disposed on a diameter line of the equator plane. In relation to the image plane of FIG. 6, the light source 3 is disposed offset toward the back and is in turn preferably provided on a diameter line, together with a light source 4, which is not shown here.

When viewing the light sources perpendicularly from above, for example from the view of the camera K, it is apparent that they are disposed in a plane at a distance from the center of the scattering body marked by a cross and, for example, at the corners of a preferably equilateral triangle or at the ends of a cross, which preferably has the shape of "+" or "X".

Figure 6:
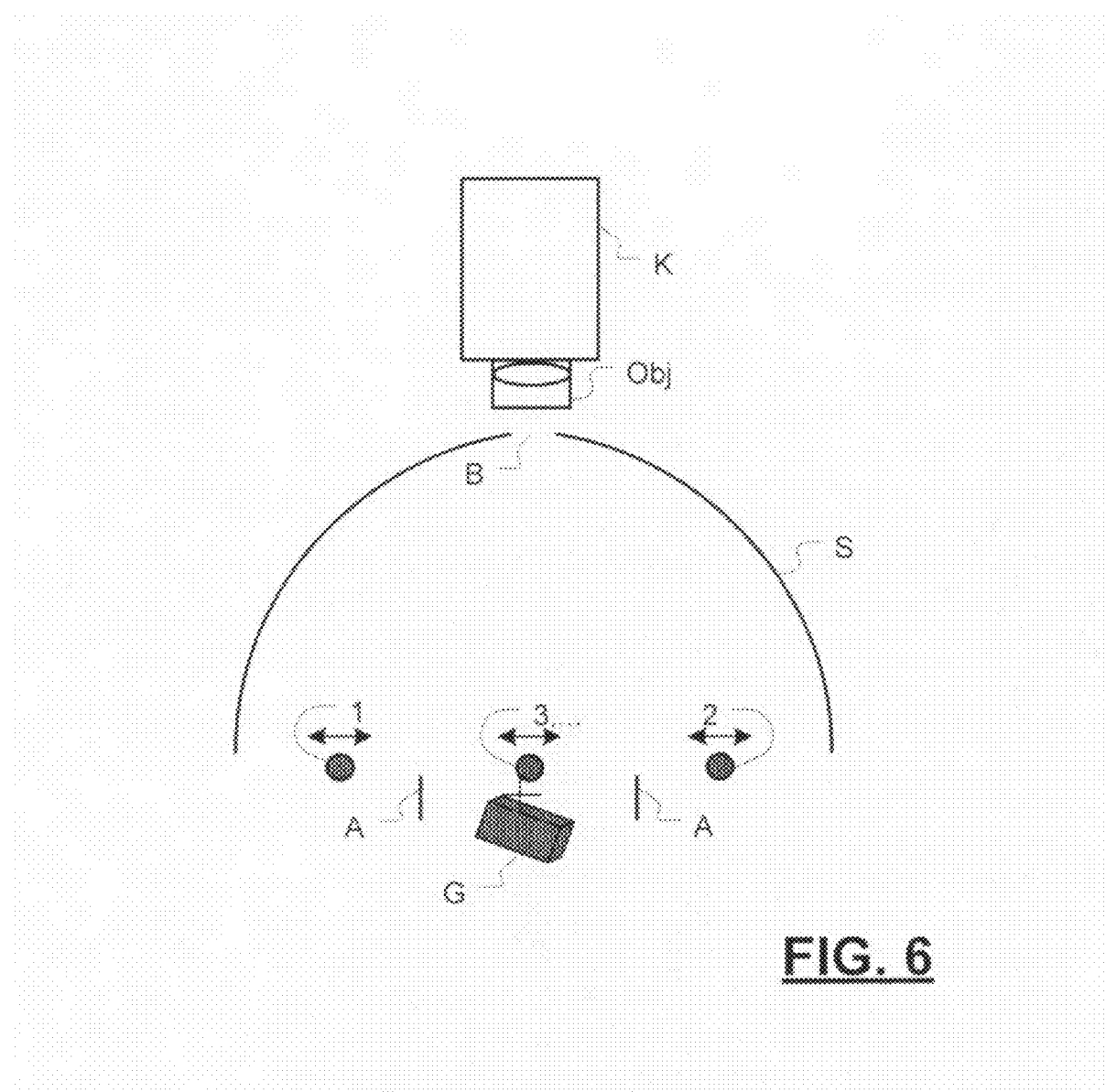
FIG. 6 illustrates a device with illumination on an inside of an opaque scattering body.

In FIG. 6, in the optical path between the light sources 1 and 2 on the one hand and the object G on the other hand shadows A are provided, which prevent direct illumination of the object. In FIG. 6, the shadow associated with the light source 3 is not shown for simplicity reasons.

The configuration of the shadow A illustrated here, which is also provided in other embodiments, is arbitrary. The crucial aspect is to prevent direct illumination of the object by the light source. It is therefore possible to provide the shadow on the mount of a light source or on the mount of the object. Finally, also separate mounts for the shadows may be provided.

By selecting the parameters in this way, all points of the scattering body can be encoded across a large area. The type of encoding and the illumination distribution substantially correspond to external illumination from a large distance, although the light sources in fact illuminate the scattering body on the inside from a small distance. As a result, the inclination can be calculated with the method known from WO 2004/051186.

Alternatively, the light sources however may also be disposed in the vicinity of the equator and shine on the opposite side of the scattering body on the equator. In this case, the points of the scattering body removed from the sources can be illuminated more brightly than those close to the sources. For objects with primarily scattering surfaces or a combination of shiny and scattering surfaces, additionally direct illumination of the object may be expedient. For this purpose, light sources can be attached, for example, to the inside of the scattering body or protrude into the inside through orifices, the light direction preferably being toward the object.

In all the above cases, it may be advantageous to mount the light sources displaceably so as to be able to vary the position as a function of the application (FIG. 6).

With respect to question 2, excellent illumination is achieved because the light can reach the inside of the scattering body everywhere. No optics for bundling the light are required (question 3).

The camera may advantageously be disposed directly outside of the scattering body, so that no shadowing occurs (question 4).

The sight opening can then be kept to a minimum (question 5).

All non-transparent materials, such as metal, plastic and the like, are materials that can be used (question 6).

Cleaning is generally not required since the inside of the scattering body is protected from soiling and contact. Damage can likewise be largely excluded (question 7).

In addition, this configuration of the light sources offers further advantages. It is possible to ensure that the user of the device is not blinded by one of the light sources. This is particularly important for high-performance light sources, such as powerful LEDs, for which potentially laser protection regulations may apply. In addition, falsification of the measurements by ambient light is prevented.

Furthermore, the device is preferably configured as follows.

Camera

It is preferred if an electronic camera, particularly a CCD or CMOS camera, is used as the camera. The images can be transmitted to an electronic processing unit for further processing or can be processed directly in an intelligent camera. Both matrix cameras and line scan cameras may be used.

Lens

The lens is preferably configured as a macro lens because the object is preferably disposed a short distance from the lens. Likewise, a plurality of cameras with a plurality of lenses may be used. Micro lenses are also conceivable, if very high enlargements are required.

Scattering Body

The scattering body is preferably configured as a hemisphere, sphere, a semi-cylinder, cylinder, ellipsoid, cube, a free-form surface or parts thereof (FIG. 6). When a matrix camera is used, a hemisphere is preferred, when a line scan camera is used a semi-cylinder or a hemisphere is preferred.

Figure 7:
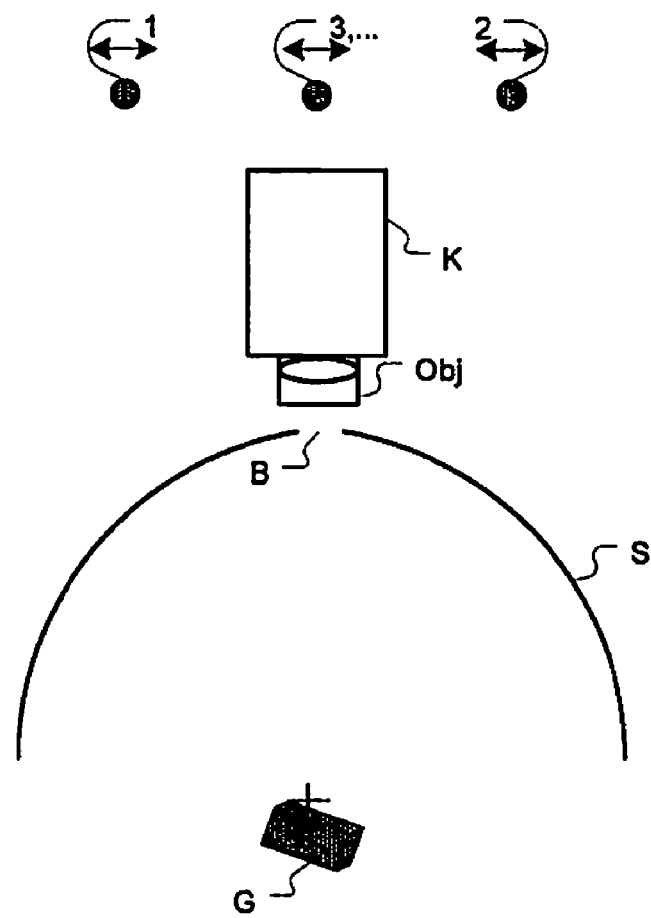
FIG. 7 illustrates a device with illumination by light sources outside of a transparent scattering body.

The scattering body of known devices may be made of transparent material, such as frosted glass, matt transparent plastic and the like, when illuminated externally (FIG. 7). According to the invention, however, opaque materials such as metal, opaque plastic and the like are used (FIG. 6). The scattering body may be uncoated, for example it may have a rough and consequently diffusely scattering surface. It is preferably if it is coated with a diffusely reflecting color, which scatters incident light non-directionally. The preferred color is white, however other colors are possible as well. It is particularly advantageous if the color has fluorescent or phosphorescent properties. The material of the scattering body may also have this property, and in this case a coating is not absolutely required. In this way, light with preferably short wavelengths, such as blue or ultraviolet light, can be converted into light with longer wavelengths, particularly also white light. It is particularly advantageous to equip the camera and/or the lens with a blocking filter for certain wavelengths, preferably for small wavelengths. In this way, direct incidence of light from the light source in the camera is prevented, however the light scattered by fluorescence or phosphorescence is allowed to pass.

The inside of the scattering body is illuminated by one or more light sources. The object G is preferably disposed at or close to the center of the scattering body. The preferred shape of the scattering body is a hemisphere. For simpler designation, also the term 'north pole' is used for the apex of the hemisphere and the term 'equator' for the edge of the hemisphere. So as to be able to displace the object G in one movement easily along the equator plane into the center of the scattering body, it is advantageous to allow the scattering body to reach from the north pole only to a region slightly north of the equator, at least in the region where the object is to be inserted.

For the camera and the lens, which are preferably provided outside of the scattering body, the scattering body may comprise an orifice B referred as a sight opening, which enables a view of the object (FIG. 6). The orifice B also acts as a diaphragm for the lens. The orifice B should be configured large enough that it enables an unobstructed view of the object to be examined or parts thereof. A large orifice allows a lot of light to reach the camera. This is particularly desirable for short exposure times. In addition, the diffraction-limited resolution increases with a wide orifice. On the other hand, the orifice B should be as small as possible so that the largest possible part of the scattering body surface remains usable. At the same time, the depth of field range can be expanded with a small orifice B, so that also objects G with large differences in height can be clearly depicted everywhere. These requirements can be reconciled if the position of the orifice B and the position of the entrance pupil EP of the lens are identical. Optionally, for technical reasons, it may also be advantageous to place the plane of the orifice B only in the vicinity of the entrance pupil EP. This is particularly the case if the position of the entrance pupil is not physically accessible because it is located inside the lens. The diameter of the sight opening is preferably selected equal to or smaller than the diameter of the entrance pupil of the lens, so that the least amount of surface of the scattering body remains unused. If the diameter of the sight opening is smaller than that of the entrance pupil of the lens, the sight opening represents the aperture diaphragm of the entire optical system, comprising the lens and the sight opening. Particularly in the case of wide opening of the camera diaphragm and a small sight opening, the position of the entrance pupil EP of the overall system can be forced to the position of the sight opening.

A further advantageous effect contributes to the fact that the usable surface of the scattering body can be as large as possible. First, it is assumed that the object is very shiny and can be considered a level mirror disposed in the equator plane. The lens is focused on the mirror, which is to say the equator plane. In the mirror, the sight opening is visible, but blurred. The question is how large the circle of consuion is. Based on symmetry deliberations, the conclusion is that the diameter of the circle of confusion corresponds precisely to the diameter of the entrance pupil of the overall optical system, which is to say the sight opening. The edge of the sight opening then becomes blurred into the center of the sight opening, quasi as if the scattering body did not have any orifice at all. This effect is further reinforced if the focus is directed at a plane slightly north of the equator, thus making the circle of confusion larger than the sight opening and guaranteeing certain overlap. So far, a mirror was assumed to be the object, which supplies a clear picture. In the case of rougher shiny surfaces, the image of the sight opening blurs even further, and for diffusely scattering surfaces it disappears completely. It is advantageous if the sight opening of the scattering body is configured as an exchangeable insert. In this way, a larger or smaller sight opening can be used, as needed.

As an alternative to the circular sight opening, variants are conceivable, which expose only a portion of the circular surface. Examples include one or more sectors of a circle. Subdivisions in a radial direction are also conceivable, preferably combined with sectors of a circle. Other shapes, however, are also possible, for example a hole eccentric with respect to the optical axis of the lens all the way to arbitrary shapes. The sight opening is preferably configured such that it cab be rotated about the optical axis of the lens, for example as a rotatable spherical cap, which is inserted flush in the scattering body. During exposure of the camera image, the rotating sight opening can then pass over the entrance pupil of the lens. It is particularly advantageous if the sight opening during an exposure passes over the entrance pupil precisely once, twice or with a further integer multiple, achieving uniform exposure inside the entrance pupil.

Figure 8:
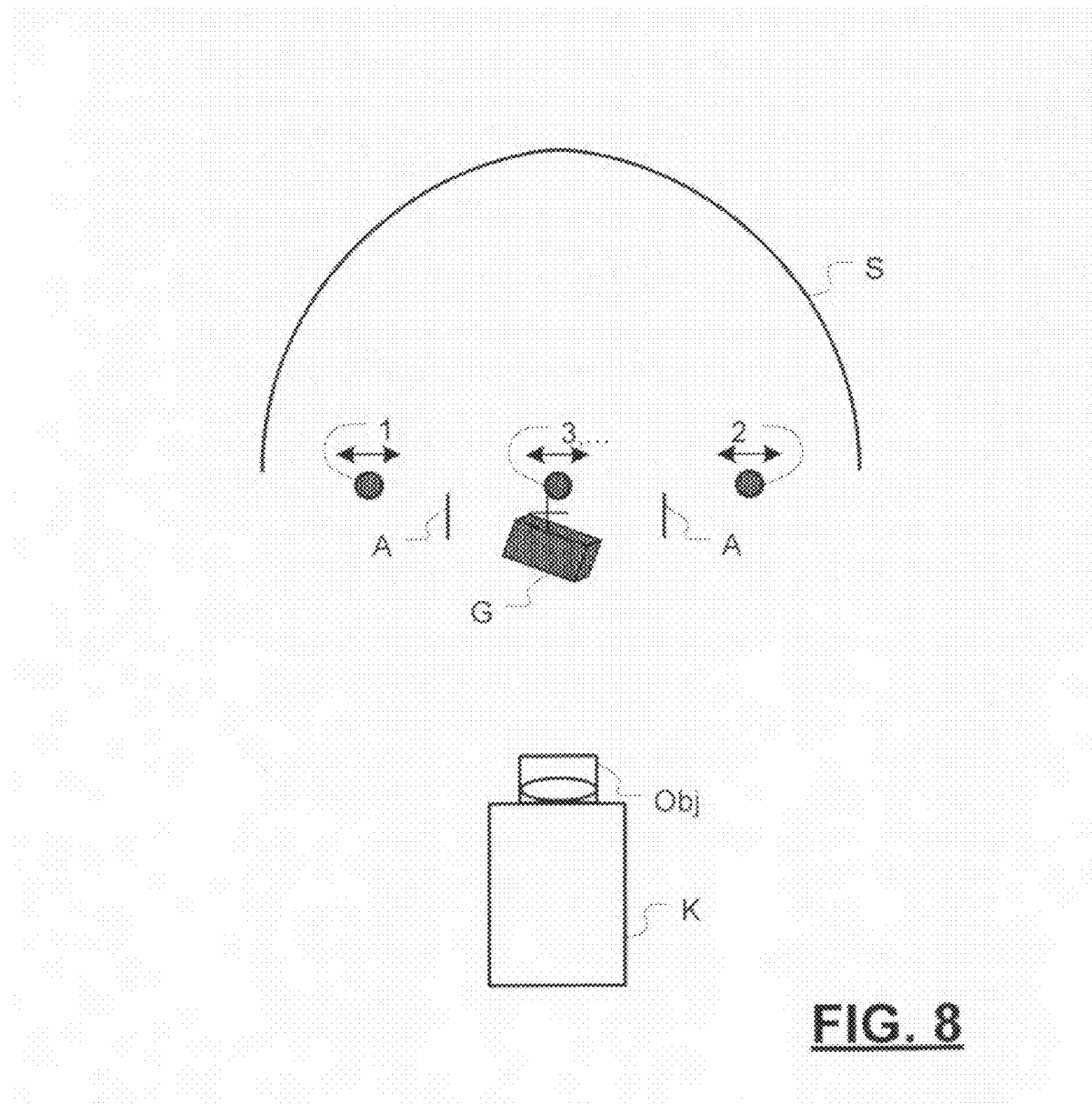
FIG. 8 illustrates a device associated with a transparent object and having a scattering body without a sight opening.

If a transparent object is to be examined, for example one made of clear glass, plastic, and the like, the camera with the lens is preferably disposed facing north from the south pole. The camera views the scattering body through the body to be examined (FIG. 8). In this case, a sight opening is not absolutely necessary.

Light Sources

Possible light sources include, for example, filament bulbs, gas discharge lamps, light sources with optical fibers, flash lamps, laser light sources as well as semi-conductor radiation sources. Particularly light-emitting diodes (LEDs) are of interest because they are small in size, can be quickly switched and have a long service life. Particularly high-performance LEDs with high radiation capacity are advantageous. The light sources can be switched on independently from one another and create different lighting situations. The light sources, or also groups of light sources, can be switched independently from one another. Depending on which light source or group of light sources is switched on, the lighting situation changes. The goal is to dispose the light sources 1, 2, 3 . . . such that all positions on the surface of the scattering body can be encoded. So as to encode this surface, for example starting from a point of the equator along a line toward the north pole and then on to the opposite point of the equator, continuously increasing or decreasing illumination along this line is desirable. This is advantageously achieved in that the light source is disposed outside of the center of the scattering body, preferably in the equator plane, at least close to the equator plane, the light direction being perpendicular thereto. Other possible orientations of the principal ray of a light source were already explained in more detail above. The closer the light source is disposed to the center, the more uniform the distribution will be; the further toward the edge it is disposed, the less uniform the distribution will. For encoding, the largest possible differences between the illumination of one end point of the line and the other are desired, however the transition should be as smooth as possible. At the same time, the light source should expose the largest possible area at the center of the scattering body for the object to be examined. A good compromise with respect to all these criteria is achieved if the light source is disposed approximately 20% to 80%, preferably approximately 30% to 70% of the distance between the center of the scattering body and the inside surface thereof, in this case of the sphere radius. Particularly positions in the range of 50% are advantageous (FIG. 6).

Alternatively, a light source may also be disposed in the vicinity of the equator and irradiate the opposite side of the scattering body. In this case, the points of the scattering body removed from the source can be illuminated more brightly than those close to the source.

In all the above cases, it may be advantageous to mount the light sources displaceably and/or rotatably so as to be able to vary the position as a function of the application (FIG. 6). Upon a displacement and/or rotation of the light sources, it is preferably ensured that the symmetrical configuration is maintained.

For objects with primarily scattering surfaces or a combination of shiny and scattering surfaces, additionally direct illumination of the object may be expedient. For this purpose, light sources can be attached, for example, to the inside of the scattering body or illuminate the inside of the body or protrude into the body through orifices, the light direction preferably being toward the object.

In addition to the position of the light source and the resulting distance to every position of the surface of the scattering body, the respective inclination of the scattering body surface to the illumination direction and the radiation characterstics of the light source as a function of the different spatial directions play a crucial role. Advantageous are, for example, the spherical shape of the scattering body, wherein the inclination of each surface point is different and unambiguous encoding is possible. At the same time, the transition of the inclination from one point to another is smooth, so that the brightness level can increase or decrease evenly. An advantageous radiation characteristics of the light source is the Lambert or another wide radiation characteristic, since in the case, starting from the equator plane, for example the entire northern hemisphere can be illuminated. Alternatively, laterally irradiating light sources could be used, which are positioned, for example, in the vicinity of the scattering body surface.

A second light source can be disposed symmetrically with respect to the center of the scattering body. In the case of two light sources, the scattering body surface can be encoded along one direction, along an imaginary direction from one equator point to an opposite equator point. Therefore, only one direction of inclination can be measured.

If three light sources are used, these may preferably be disposed at the corners of a equilateral triangle, however other configurations are possible as well. When three light sources are used, two directions can be encoded on the surface of the scattering body. Three light sources thus represent the minimum number of sources, with which the scattering body surface can be encoded.

For the light sources addressed here the same information as above applies accordingly: They are disposed in one plane, which corresponds, for example, to the equator plane of a scattering body or which is diposed parallel thereto at a distance. The triangle comprises a center, which is located on a line that intersects the center of the scattering body and is disposed perpendicularly on the equator plane of the scattering body.

It is particularly advantageous, however, if four light sources are used, which—viewed from above—are disposed in the shape of an "X" or "+". In this configuration, two sources are always disposed opposite from one another. For example, such a pair can be activated if only one encoding direction is of interest; if both directions are desired, the other pair is activated as well. This configuration is also advantageous for feeding the objects to be examined because it offers more space than, for example, the symmetrical arrangement of three sources. A larger number of light sources is likewise possible, but not absolutely necessary.

If four light sources are used, in principle the explanations from above apply: The light sources are disposed in a plane that corresponds to the equator plane or is provided parallel thereto. The light sources are disposed opposite from each other in pairs and are preferably disposed symmetrically. If configured in the shape of across, be it the shape of an "X" or a "+", the center of the cross is located on a line that intersects the center of the equator plane and is disposed perpendicular thereto. A possible position of the light sources mentioned so far has been the equator plane. To allow easy feeding of the parts to be examined, however, it may be expedient to dispose the sources in a different plane, for example further north, so as to leave the equator plane completely available as a measurement plane.

In order to prevent directly incident light of the light sources on the object to be examined, shadows A may be required, which are connected, for example, to the mounts of the light sources or a retainer of the object to be examined. It is also possible to provide separate mounts for the shadows A. The shadows A should be selected large enough so that no direct light shines in, however at the same time as small as possible so that, viewed from the object, no part of the scattering body is covered.

The scattering body S may comprise a cylindrical projection in the region outside of the orifice B, the projection serving as a mount for various diaphragms to implement different sizes and shapes of the sight opening (orifice B) and for the camera.

Stereo System

Figure 9:
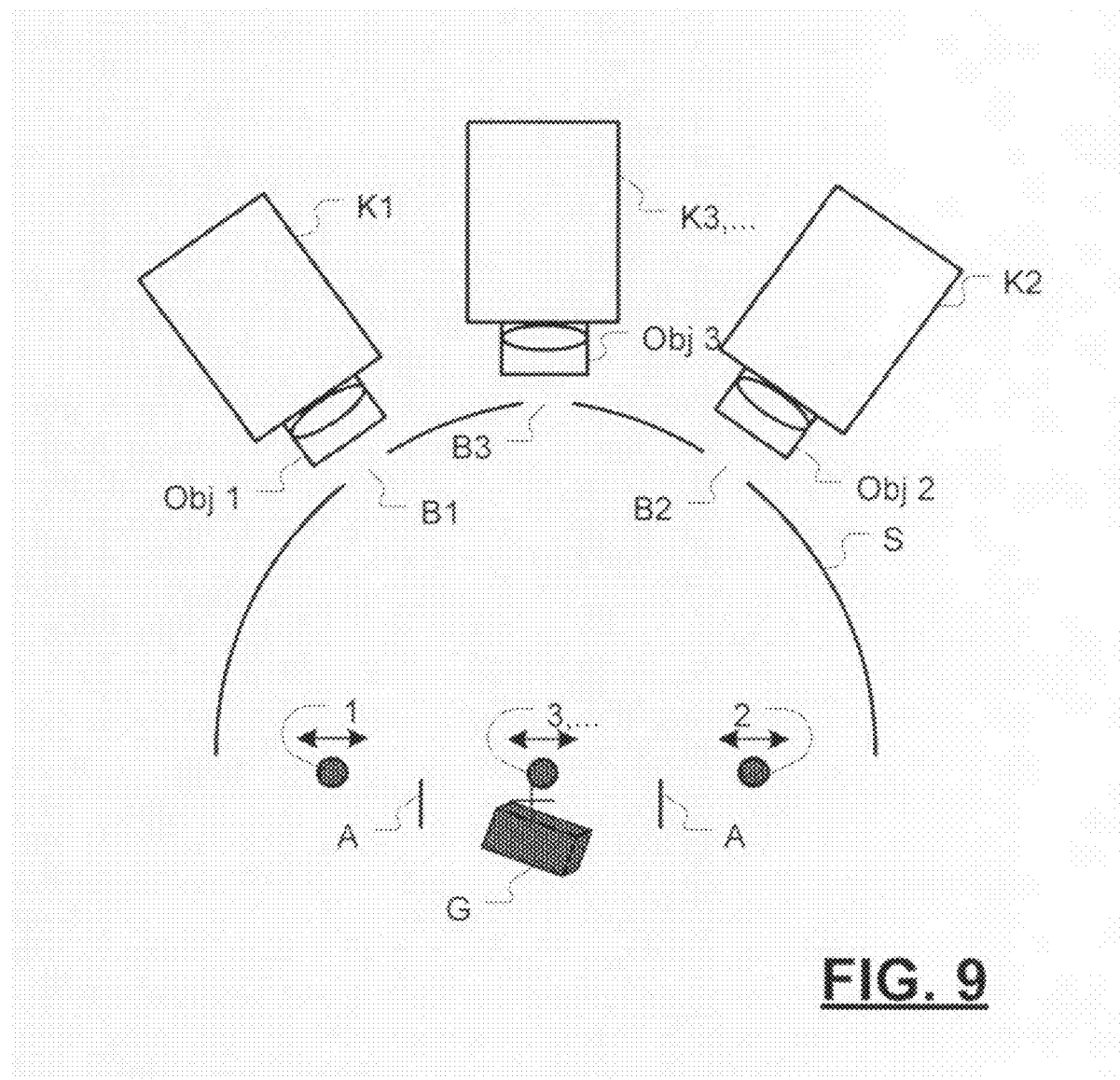
FIG. 9 illustrates a device with a plurality of cameras and a corresponding plurality of sight openings in a scattering body.
Figure 10:
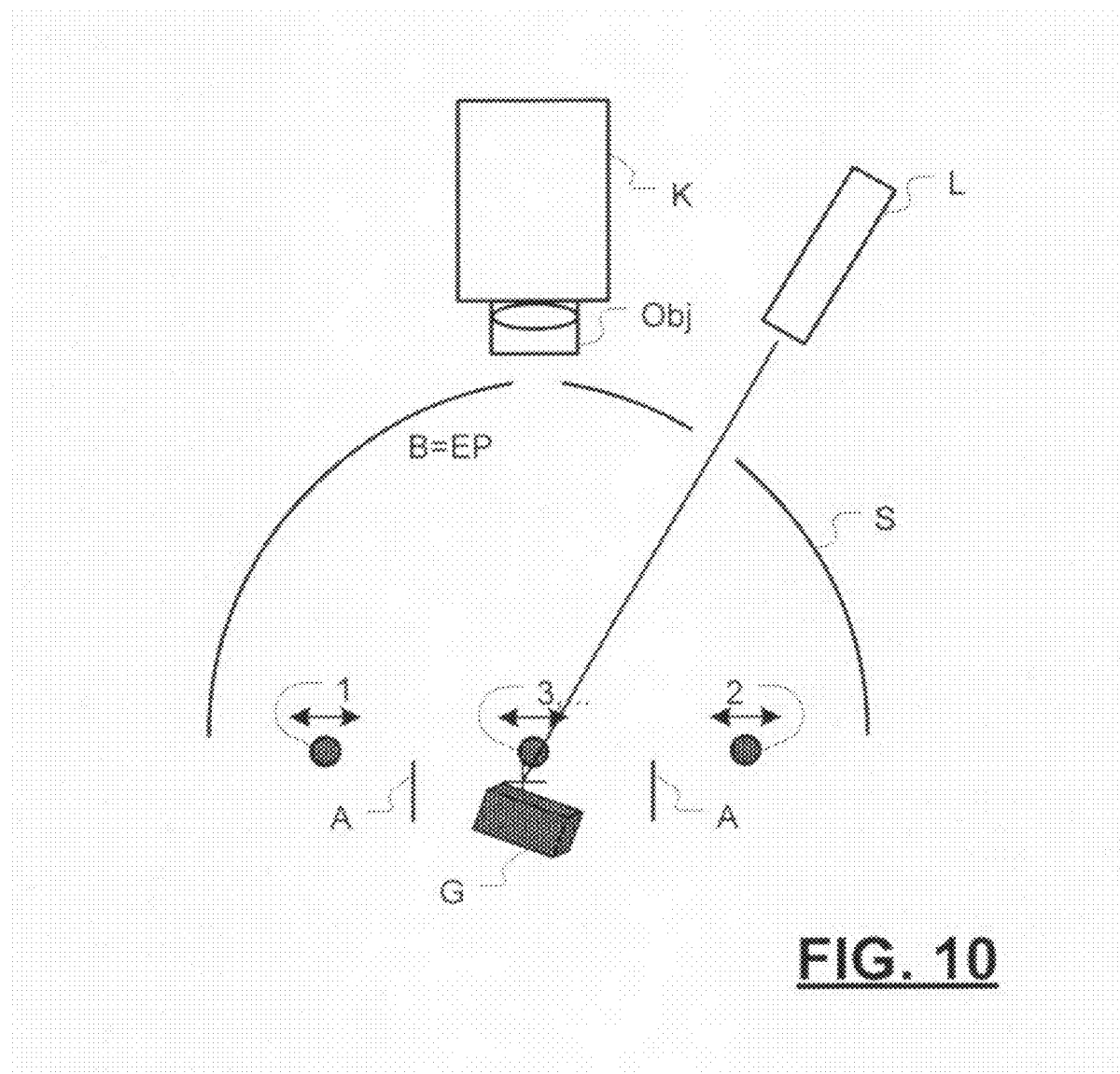
FIG. 10 illustrates the device of FIG. 6 with a line projector.

In addition to the number of the light sources, also the number of cameras and/or lenses can be varied (FIG. 9). If two cameras are used, for example, the device may be used to carry out a binocular stereo method. It is preferably if two sight openings are provided for the two cameras or lenses, the openings allowing a view in the direction of the object to be examined from two different positions. The disparity of corresponding points in the two camera views provides information about the position of object points with respect to the third dimension, which is to say perpendicular to the equator plane. The binocular stereo method is a method for measuring heights, while photometric deflectometry is used to measure inclinations. Both methods are advantageously combined, for example as described in U.S. Pat. No. 6,590,669. The height-measuring method offers advantages with respect to the measurement of the global three dimensional shape of the object, and the inclination-measuring method is beneficial for measuring the local three dimensional shape. The number of the cameras may be further increased, for example to three or four cameras.

Particularly a device comprising a higher or identical number of cameras as light sources offers the advantage that a separate camera is available for each light source, which may enormously reduce the recording time for the images (FIG. 9). Typical electronic cameras (such as CCD and CMOS cameras) exhibit large differences between the minimum exposure time and the minimum time required for the entire image cycle, including reading of the image sensor. The exposure time can be easily set to values under 100 microseconds, while for the entire image cycle times over 10 milliseconds are common. This is due to the fact that considerably more time is required for reading the image sensor and transmitting the data than for the actual exposure. If a single camera is used, the time required for the image cycle is crucial because the same camera must record multiple images consecutively. If the number of cameras is identical to the number of light sources, the mere exposure time is crucial. The imaging process would be started in the cycle of exposures with a very brief delay, which is referred to as a trigger cascade.

Combination With Other Height-Measuring Methods

Alternatively, the device may also be used to combine photometric deflectometry with a height-measuring method other than the binocular stereo method, for example fringe projection, interferometry, white light interferometry, a time-of-flight method or preferably the laser cutting method (FIG.

Figure 11:
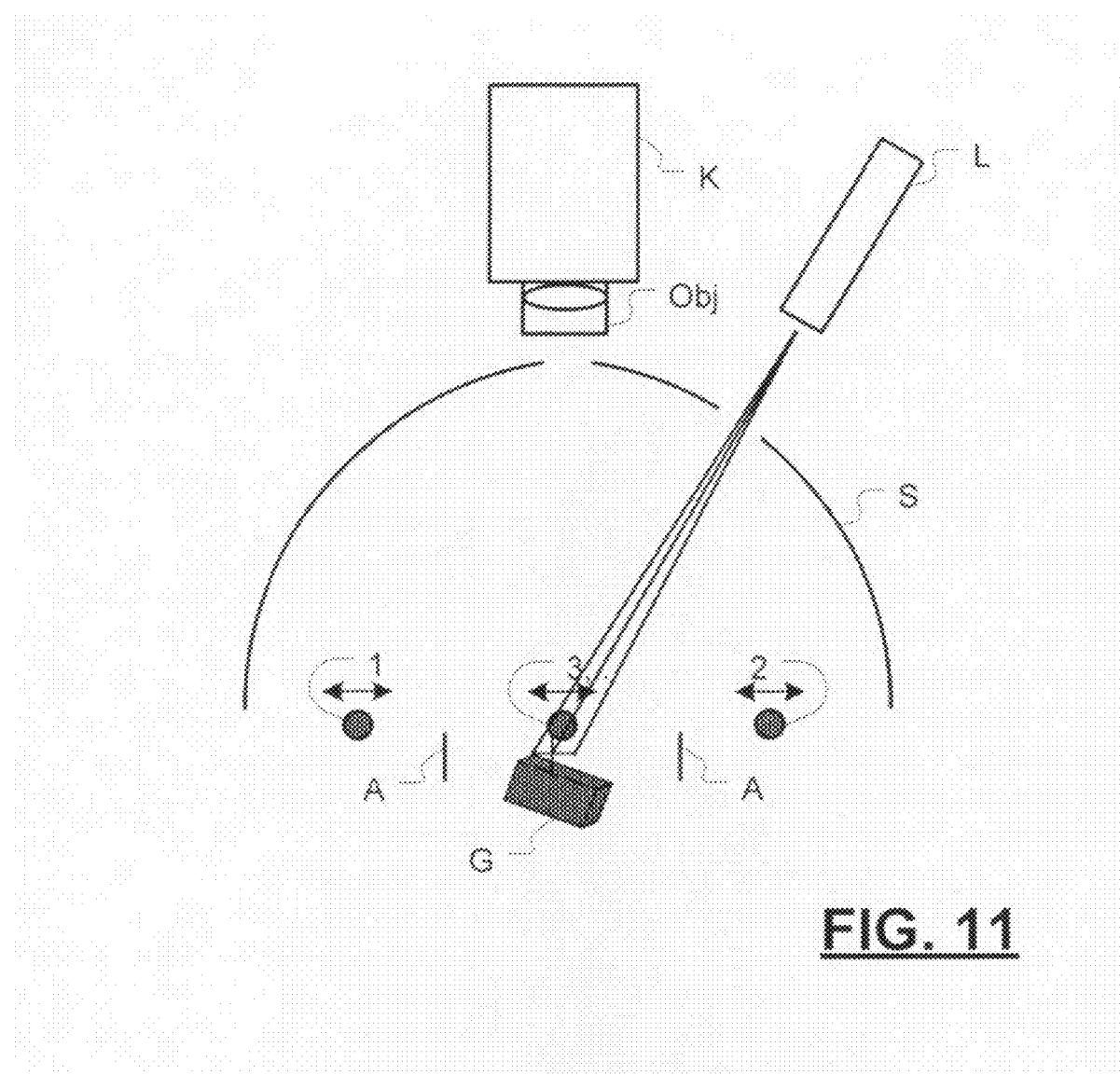
FIG. 11 illustrates the device of FIG. 10 with a line projector and multiple projected lines.

10). For this, preferably a sight opening is provided in the scattering body for the illuminating laser. Semi-conductor lasers L are particularly preferred, in particular such in which optics for producing one or more laser lines are already integrated. Such light sources are very compact and can be electronically switched with extremely short time delay. Laser cutting methods typically operate with a mechanical system, which displaces the test object and an individual laser line relative to each other, thus scanning the test object consecutively section by section. For each section, an individual camera image is required, which takes accordingly much time. The disadvantage is also that a precise displacement unit, which is synchronized with the camera images, is required. It is therefore advantageous if a plurality of laser lines are projected simultaneously (FIG. 11). In this way, a plurality of sections of the object to be examined can be measured simultaneously, for example 10 or 20 sections. In the inventive combination with photometric deflectometry, a single camera image may already be sufficient so that the displacement unit and the additional time are not required. This is possible because the height-measuring method must only supply global shape data, while the local shape data is provided by photometric deflectometry.

Calibration

Figure 12:
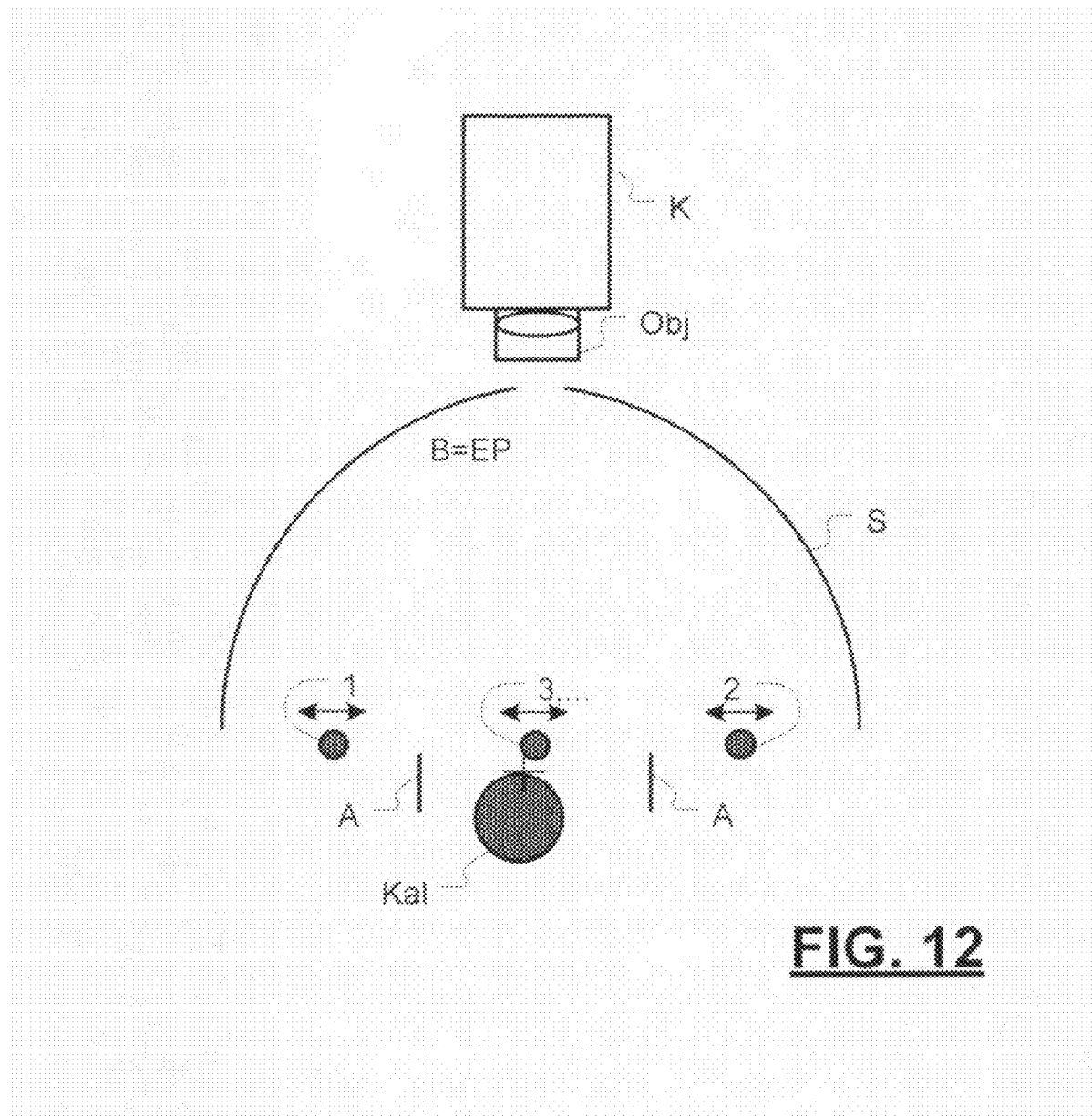
FIG. 12 illustrates a device with illumination on an inside of a scattering body and including a calibration object.
Figure 13:
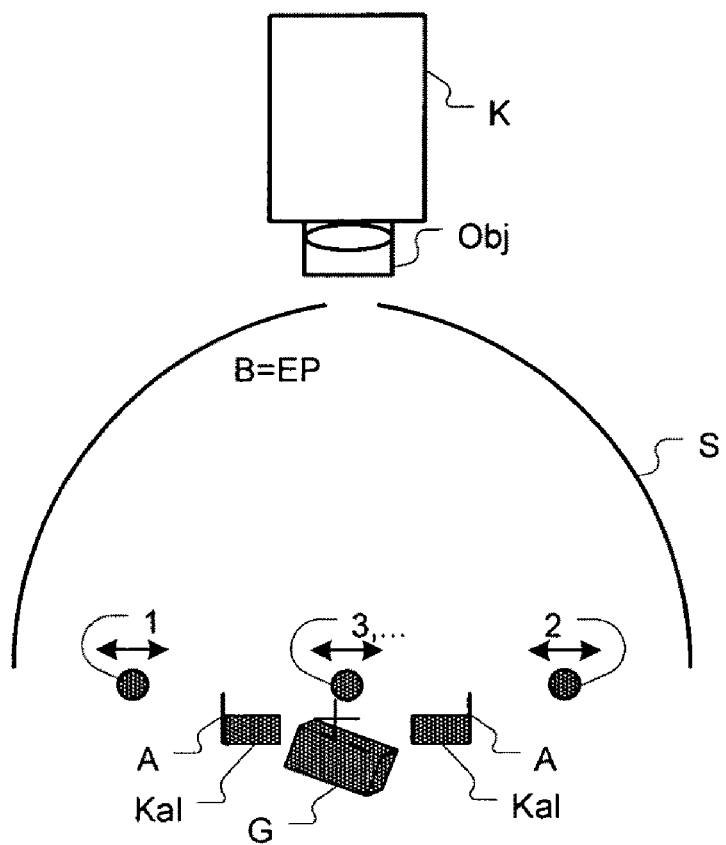
FIG. 13 illustrates a device with illumination on an inside of the scattering body and operatively associated with a calibration object during examination of an object.

The device according to the invention may be supplemented by a calibration object Kal (FIG. 12). The object is used to compare the measured inclination values to the true inclination values based on a known reference object. In this way, it is possible, among other things, to compensate for tolerances of the spatial illumination distribution of the light sources, the radiation capacity thereof, the position and orientation thereof, the shape and position of the scattering body, the radiation characteristics of the surface or coating as well as the position and orientation of the camera. Possible reference objects include objects with known shapes, particularly such that comprise a reflective surface and have a large number of different inclinations. A shiny metal sphere manufactured with precision is preferred, because here all possible inclinations occur. If matt or partially matt objects are examined, it may be advantageous to provide a matt calibration object, for example a matt or partially matt sphere. For this calibration object, the inclination values are measured across a large area and then compared to the known values. The allocation of measured values to the actual values is the calibration process. In addition, it is possible to monitor the calibration process also during the examination of objects, particularly by a possible variation of the radiation capacity of the light sources. For this, in addition to the test object, a reference object may be introduced in the field of vision of the camera (FIG. 13), for example a level specular surface or a specular sphere, a completely or partially matt surface or sphere. Other shapes and surface properties are possible.

Figure 14:
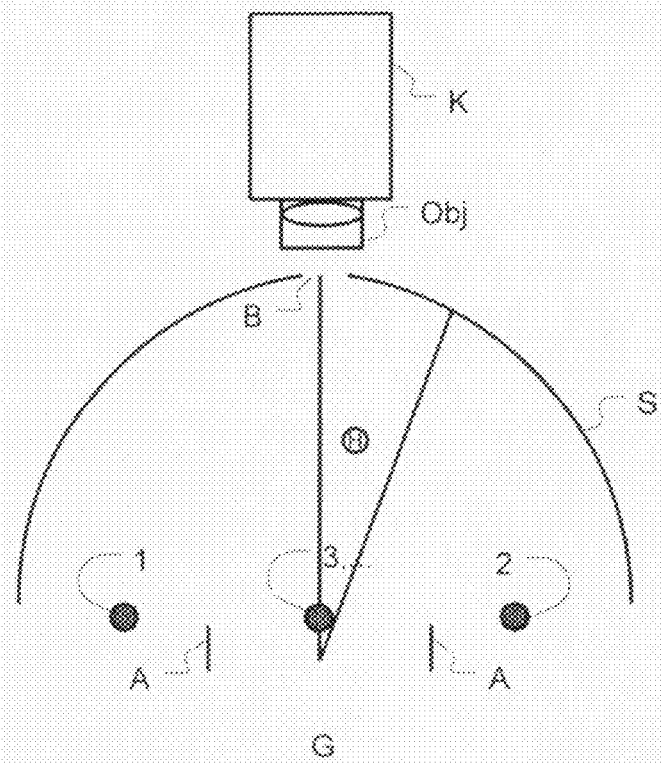
FIG. 14 illustrates an example of an illumination distribution on an inside of a scattering body.
Figure 14:
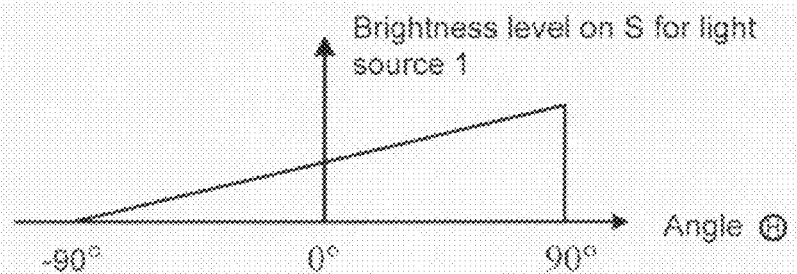
Figure 14:
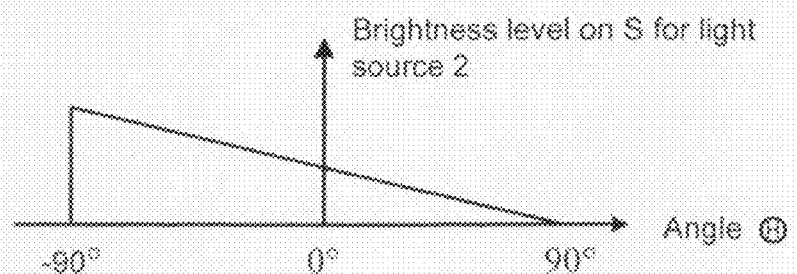

FIG. 14 shows an example of an illumination distribution on the scattering body S along an imaginary plane through the light sources 1 and 2. Horizontally, the angle θ measured from the north pole is shown. The vertical axis represents the brightness level on the inside of the scattering body S for the respective light source 1 or 2.

The second illustration from below shows the brightness level for the light source 1. If the source is activated, the brightness level increases steadily for an angle θ from −90° to 90°.

In the illustration at the bottom, the brightness level on the inside of the scattering body S for the light source 2 is shown. It is apparent that the brightness level decreases steadily for an angle θ from −90° to 90°. As a result, points on the scattering body S with different angles θ are encoded and differentiated.

As explained above, the light sources are switched on and off in a time sequence, so that consecutively a plurality of different lighting situations are created. This enables the encoding and differentiation of the points on the scattering body S addressed here.

From the explanations for the above figures it is apparent that the shape of different objects and surfaces can be measured. In the exemplary embodiments shown here, the camera K is disposed above the object G, to the extent that, as explained above, transparent objects are analyzed.

It is also possible, however, to use the device for optically measuring the shape of objects and surfaces described herein to analyze exterior or circumferential surfaces of objects, or also the interior surface of recesses in objects.

For the measurement and analysis of circumferential areas on cylindrical or substantially cylindrical objects, a specially shaped mirror Ko is used, which has the shape of a cone. The camera as well as the inventive test device are aimed at the face of the object to be examined. By means of a mirror comprising a conical inside surface that tapers—viewed from the camera—in the direction of the object, the exterior surface of the object, in this case the circumferential area of a cylindrical or substantially cylindrically object G can be analyzed. To the camera, this area appears as a circular ring, which surrounds the face of the component. It is therefore possible to analyze the face and the circumferential area of an object in the same view.

With the help of the mirror described here, the circumferential surface can be easily analyzed. With conventional methods, the face and circumferential area of an object would have to be analyzed separately. In addition, a relative rotation between the camera and object would have to be performed, for example a rotation about an axis, to scan the circumferential area. The circumferential area can then be scanned with the help of a line scan camera, for example.

With the help of conical mirrors, it is also possible to inspect recesses, particularly cylindrical or substantially cylindrical bores. For this, a mirror comprising a conical exterior surface is used, the surface tapering in the direction of the camera.

Figure 15:
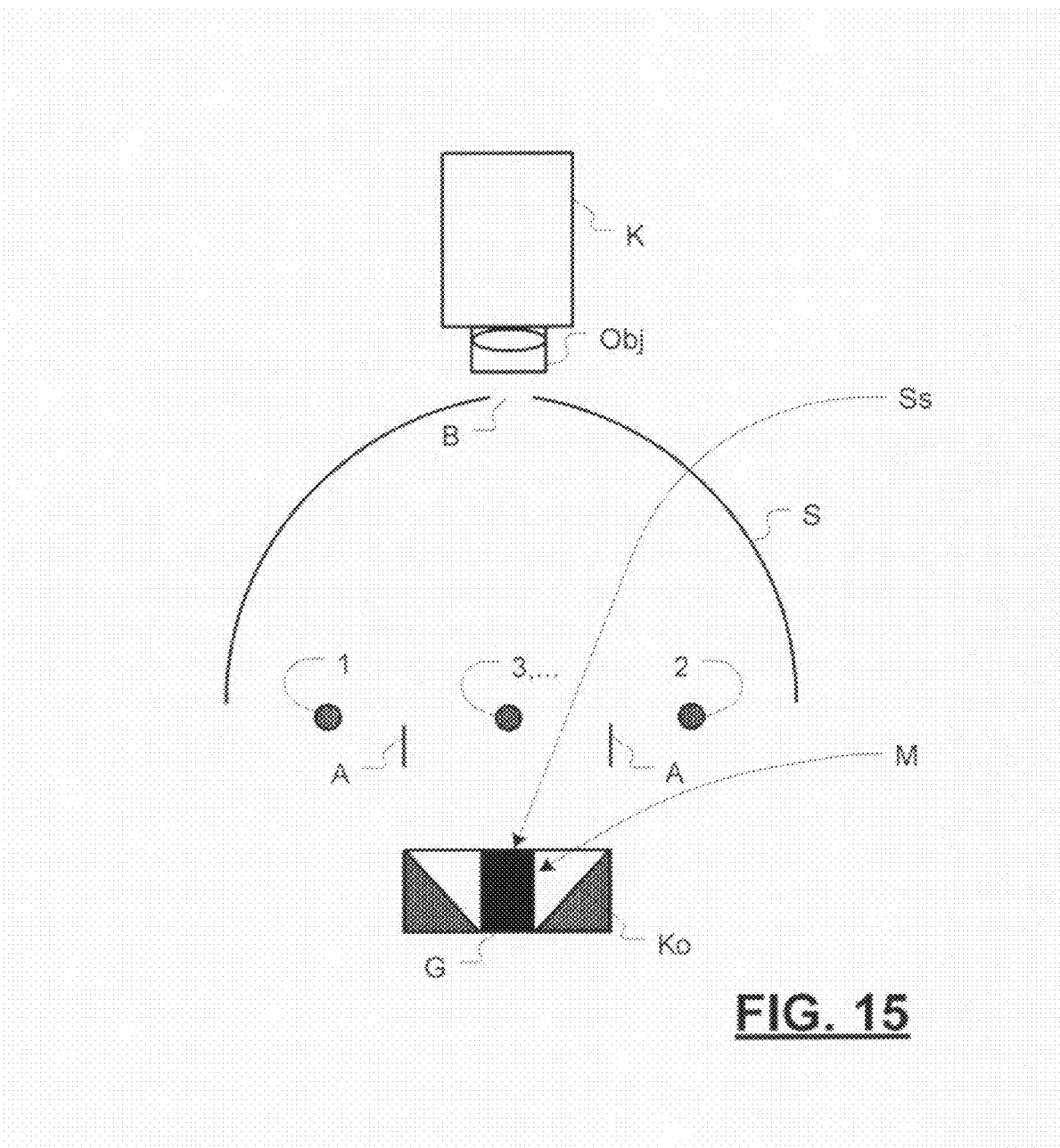
FIG. 15 illustrates an example of the device of FIG. 6 configured to inspect circumferential areas of a cylindrical object.

FIG. 15 shows a first exemplary embodiment of a device for inspecting circumferential areas on cylindrical or substantially cylindrical objects.

The basic setup of the device corresponds to that explained above. Inside a scattering body S, the object G is provided. It is illuminated by at least one light source. Here, three light sources 1, 2 and 3 are illustrated, as well as the above-described shadow A, which prevents direct illumination of the object G. The cylindrical object G is disposed vertically, so that the center line thereof extends through the lens Obj of the camera K, which measures the face Ss of the object G.

The object G is disposed on the inside of a specially configured mirror, here a mirror Ko with a conical interior surface, which is oriented such that the image of the circumferential area M of the object G can be captured by the camera K through the orifice B in the scattering body S. The camera consequently sees the face Ss of the object G and, as an annular surface, the peripheral circumferential area M.

In the exemplary embodiment shown in FIG. 15, the object G is provided in the annular mirror Ko with the conical interior surface.

Figure 16:
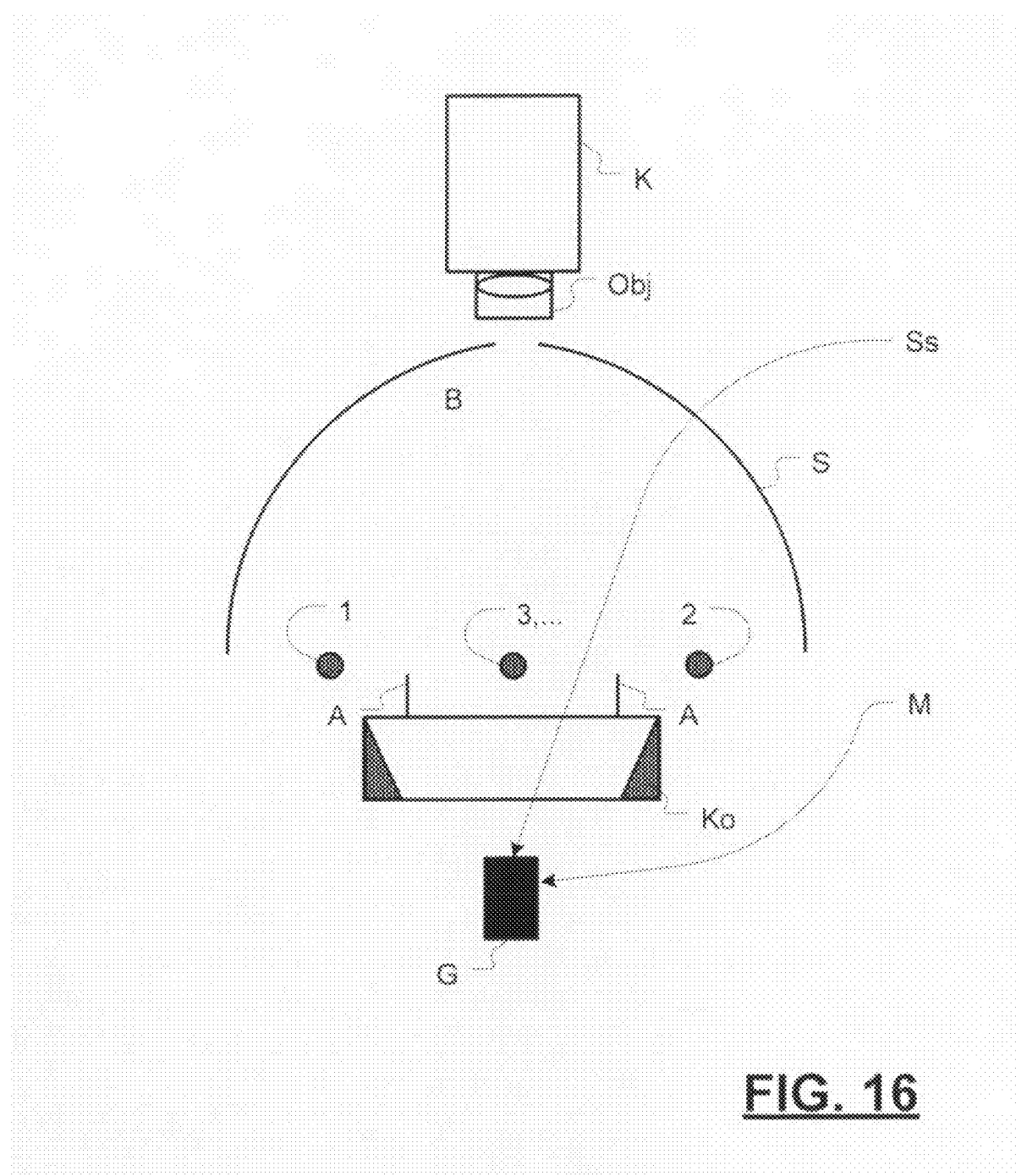
FIG. 16 illustrates an example of the device of FIG. 6 configured to inspect circumferential areas of a cylindrical object.

FIG. 16 shows a modified exemplary embodiment of the device illustrated in FIG. 15. Identical parts and parts with equivalent functions have been denoted with the same reference numerals.

The exemplary embodiment shown in FIG. 16 differs from that in FIG. 15 by the design of the specially configured mirror Ko. The inside surface thereof is likewise configured conically, however it is inclined such that the circumferential area M of the object G, which is disposed below the mirror Ko, is imaged and can be captured by the camera K. The camera consequently also captures the face Ss of the object G and, as a peripheral surface, the circumferential area M thereof.

Figure 17:
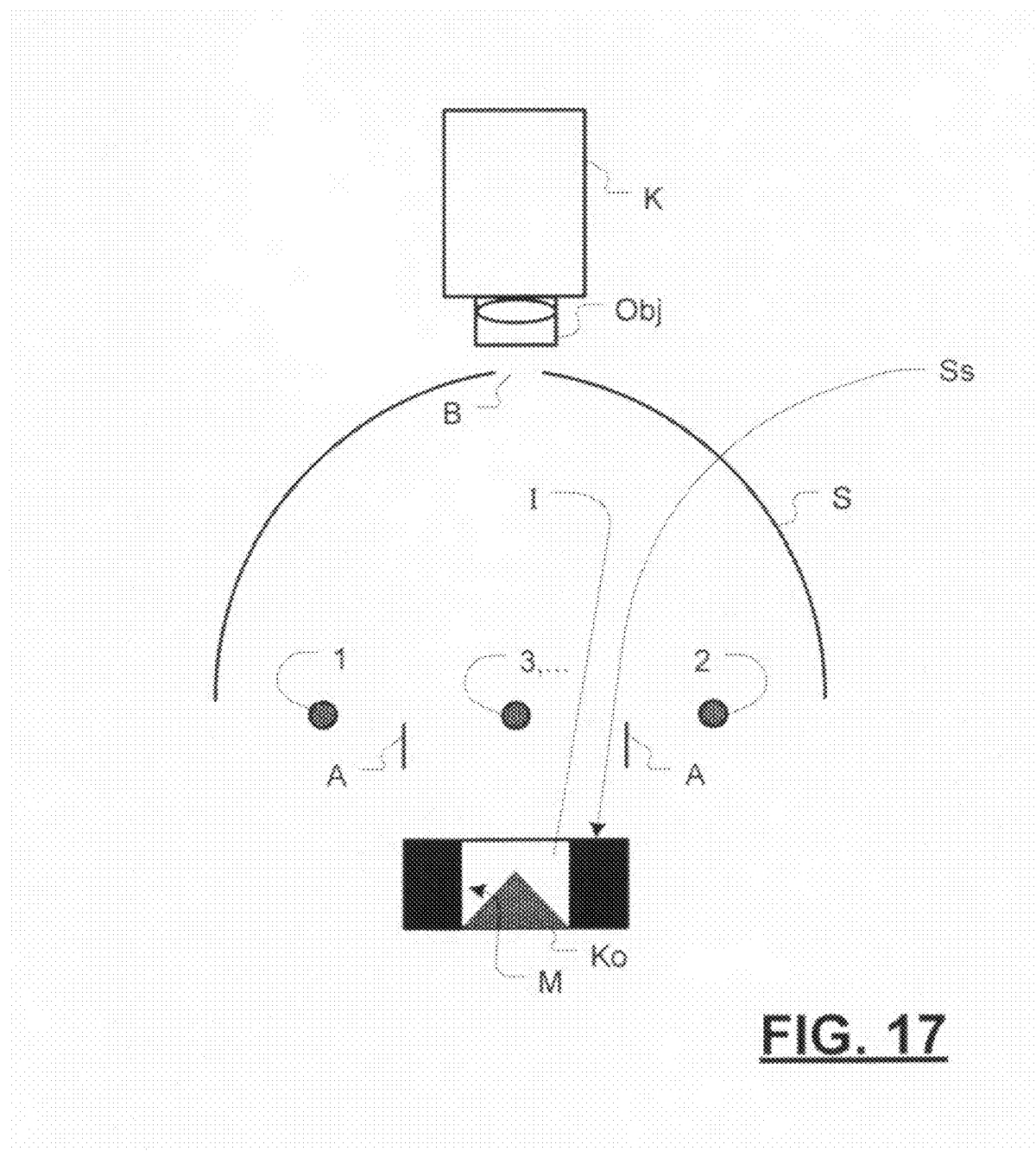
FIG. 17 illustrates an example of the device of FIG. 6 configured to inspect circumferential areas of a cylindrical object.

FIG. 17 shows a further exemplary embodiment of a device. Again, identical parts and parts with equivalent functions have been denoted with the same reference numerals, so that repetitions can be avoided. The device serves the measurement of the face Ss of the object G, but also the measurement of an inner circumferential area M.

For this purpose, a specially configured mirror Ko is inserted into the inside I of the object G, the mirror comprising a conical exterior mirror surface. The surface tapers in the direction of the camera K and therefore reflects the image of the circumferential area M of the inside I in the direction of the lens Obj.

The camera K thus measures the face Sx of the object G and at the same time a circumferential area M of an inside I of the object G. So as to obtain a clear image, a conical mirror Ko with specular exterior surface is used, which preferably serves the measurement of cylindrical or substantially cylindrical circumferential areas M.

In the exemplary embodiment shown in FIG. 17, the bottom of the object G and the mirror Ko are disposed on an imaginary common plane. In principle, however, it is possible to dispose the mirror also below the object G, provided that the angle of inclination of the conical mirror Ko is adjusted accordingly.

Furthermore, it is also possible to combine the device shown in FIG. 17 with a mirror as that explained based on FIGS. 15 and 16. In this way, in the case of annular objects G, the object's face Ss, an interior circumferential area M and an exterior circumferential area can be measured with suitable mirrors in a single image.

The mirrors Ko described here, which are also referred to as conical mirrors, comprise mirror surfaces, which are configured as inner cones (see FIGS. 15 and 16) or as outer cones (see FIG. 17).

The exemplary embodiments of the device illustrated in FIGS. 15 to 17 are characterized in that the interior or exterior surfaces of the object G to be analyzed are illuminated by the specially configured mirror Ko. It is therefore not necessary to provide additional illumination means for illuminating the inner or outer lateral surfaces of the object to be analyzed.

It is therefore apparent that the device described herein has very flexible applications, that not only the tops of objects and surfaces can be analyzed, but also outer or inner surfaces, which were referred to herein as circumferential areas M. It is also possible during a measuring operation to measure inner and outer circumferential areas together with a face Ss of an object, as was explained particularly based on FIG. 17.

It is apparent that the device overall has a very simple design, wherein advantageously the existing light sources can be used to illuminate also exterior and interior circumferential areas.

The invention claimed is:

1. A device comprising:
    an opaque scattering body defining an outer side and an inner side, the scattering body having an apex;
    at least one camera configured and arranged to look inside the scattering body;
    at least one lens configured and arranged to image within the at least one camera an object which is to be examined, the object being arranged to be illuminated by the inside of the scattering body; and
    at least two light sources arranged to illuminate the inside of the scattering body;
    wherein the at least two light sources are arranged such that:
        illumination of the scattering body by a first of the at least two light sources continuously increases a brightness level along an intersecting line when viewed in a defined direction along a variable angle θ measured from the apex of the scattering body, the intersecting line having a starting point on a centerline of the scattering body and extending between the scattering body and an imaginary plane through the at least two light sources; and
        illumination of the scattering body by a second of the at least two light sources continuously decreases the brightness level along the intersecting line when viewed in the defined direction.

2. The device according to claim 1, wherein the at least two light sources includes first and second light sources disposed opposite from one another on an imaginary diameter line.

3. The device according to claim 1, wherein the at least two light sources are disposed at the corners of one of a triangle and a cross.

4. The device according to claim 1, wherein the at least two light sources can be switched independently from one another.

5. The device according to claim 1, wherein the at least two light sources includes four light sources disposed in the shape of one of an "x" and a "+".

6. The device according to claim 1, wherein the at least two light sources have a wide emission characteristic.

7. The device according to claim 1, wherein the at least two light sources are disposed at a distance from the center of the scattering body, the distance being between 20% and 80% of the distance between the center of the scattering body and the inside surface thereof.

8. The device according to claim 1, wherein the at least two light sources are disposed in an equator plane.

9. The device according to claim 8, wherein a principal ray of at least one of the at least two light sources has an angle between −90° and +90° in relation to the perpendicular of the equator plane.

10. The device according to claim 1, wherein the scattering body has the shape of one of a hemisphere, a sphere, a semicylinder, a cylinder, an ellipsoid, a cube, a free-formed space and a part thereof.

11. The device according to claim 1, wherein the at least one camera includes a plurality of cameras.

12. The device according to claim 1, wherein the at least one camera includes at least two cameras, wherein the at least two light sources are independently switchable, and wherein the number of cameras at least corresponds to the number of independently switchable light sources.

13. The device according to claim 1, wherein the device comprises at least one sight opening, wherein the at least one camera is positioned outside the scattering body, and wherein the at least one camera is configured and arranged to look inside the scattering body through the at least one sight opening.

14. The device according to claim 1, further comprising an illumination device positioned outside the scattering body and operable to enable height measurement.

15. The device according to claim 1, further comprising an illumination device positioned outside the scattering body, the illumination device operative to project at least one line.

16. The device according to claim 1, further comprising a laser light source positioned outside the scattering body, the laser light source operable to project at least one line.

17. The device according claim 1, further comprising a laser light source positioned outside the scattering body, the laser light source operative to simultaneously project a plurality of lines.

18. The device according to claim 1, further comprising an illumination device positioned outside the scattering body and operable to enable fringe projection.

19. The device according to claim 1, further comprising an interferometric system positioned outside the scattering body.

20. The device according to claim 1, wherein at least one of the at least two light sources is adjustably mounted.

21. The device according to claim 1, wherein at least one of the at least two light sources directly illuminates the object.

22. The device according to claim 13, wherein the at least one sight opening is substantially identical to an entrance pupil of the overall optical system, comprising the at least one sight opening and the at least one lens.

23. The device according to claim 13, wherein the size of the at least one sight opening is variable.

24. The device according to claim 13, wherein the scattering body includes a sight opening, a shape of the at least one sight opening being is variable.

25. The device according to claim 13, wherein the at least one sight opening is displaceable.

26. The device according to claim 13, wherein the at least one sight opening is rotatable.

27. The device according to claim 1, further comprising a calibration device, including a reference object, positioned under the scattering body.

28. The device according to claim 1, further comprising a calibration device, having a sphere as a reference object, positioned under the scattering body.

29. The device according to claim 1, further comprising a calibration device, having a mirror as a reference object, positioned under the scattering body.

30. The device according to claim 1, further comprising a calibration device, including a level mirror as a reference object, positioned under the scattering body.

31. The device according to claim 1, wherein the scattering body comprises at least one of a fluorescent scattering body and a phosphorescent scattering body.

32. The device according to claim 1, further comprising a blocking filter disposed adjacent to the at least one camera for blocking light of predetermined wavelengths.

33. The device according to claim 1, further comprising a blocking filter for blocking the wavelengths of at least one of the at least two light sources.

34. The device according to claim 1, further comprising a mirror with at least one of a conical specular interior and a conical exterior surface, the mirror surface(s) of the mirror being configured and oriented such to reflect at least one of the interior and exterior circumferential areas of the object in the direction of the at least one camera, so that the at least one camera is able to take an image of a face of the object being directed towards the at least one camera and at least one of the interior and exterior circumferential areas of the object.

35. The device according to claim 34, wherein the mirror and the object share a common plane.

36. The device according to claim 34, wherein the mirror and the object do not share a common plane.

37. The device according to claim 1, wherein illumination of the scattering body by the first light source continuously increases the brightness level as the intersecting line is rotated away from the first light source such that the angle $\theta$ between the intersecting line and the centerline of the scattering body is continuously increased and illumination of the scattering body by the second light source continuously decreases the brightness level as the intersecting line is rotated toward the second light source such that the angle $\theta$ between the intersecting line and the centerline of the scattering body is continuously increased.

38. The device according to claim 1, further comprising at least one of a fluorescent coating and a phosphorescent coating applied to the scattering body.

39. The device according to claim 1, wherein the at least two light sources radiate light having non-uniform intensity, the intensity of the radiated light varying as a function of the cosine of the radiation angle of the radiated light.

* * * * *